United States Patent
Butera et al.

(10) Patent No.: US 7,115,620 B2
(45) Date of Patent: Oct. 3, 2006

(54) 1,3-DISUBSTITUTED-2-THIOXO-IMIDAZOLIDINE-4,5-DIONES AS POTASSIUM CHANNEL OPENERS

(75) Inventors: John A Butera, Clarksburg, NJ (US); Hassan M Elokdah, Yardley, PA (US); Theodore S Sulkowski, Wayne, PA (US); John L Primeau, Westford, MA (US); Joseph R Lennox, Berkeley, CA (US); Russell F Graceffa, Hamtpon, NH (US)

(73) Assignee: Wyeth, Madison, NJ (US)

( * ) Notice: Subject to any disclaimer, the term of this patent is extended or adjusted under 35 U.S.C. 154(b) by 55 days.

(21) Appl. No.: 10/282,540

(22) Filed: Oct. 29, 2002

(65) Prior Publication Data

US 2003/0119890 A1      Jun. 26, 2003

Related U.S. Application Data

(60) Provisional application No. 60/340,921, filed on Oct. 30, 2001.

(51) Int. Cl.
*A61K 31/415* (2006.01)
*C07D 233/42* (2006.01)
*C07D 233/40* (2006.01)

(52) U.S. Cl. .................. 514/290; 548/317.5
(58) Field of Classification Search ............. 548/317.5; 514/390
See application file for complete search history.

(56) References Cited

U.S. PATENT DOCUMENTS

| | | | |
|---|---|---|---|
| 3,461,133 A | 8/1969 | Stoffel | |
| 4,084,001 A | 4/1978 | Durant et al. | |
| 4,152,453 A | 5/1979 | Durant et al. | |
| 5,312,919 A | 5/1994 | Gulliya et al. | |
| 2003/0119889 A1 | 6/2003 | Elokdah et al. | |

FOREIGN PATENT DOCUMENTS

| | | |
|---|---|---|
| DE | 0154 819 | 4/1982 |
| DE | 219 483 A1 | 3/1985 |
| DE | 3540919 A1 | 5/1987 |
| EP | 0 718 290 B1 | 4/2002 |

OTHER PUBLICATIONS

Zankowska-Jasinska et al, "1,3-Disubstituted 2-thioxo, etc" CA 114: 75036 (1991).*
Beckert et al I, "Reaction of oxclic amidines with, etc" CA 113: 97511 (1990).*
McDonough, Stefan et al., Drug Development Research, 33, 190-202 (1994).
Lawson, Kim, Pharmacol. Ther., 70(1), 39-63 (1996).
Aguilar-Bryan, Lydia et al., Physiological Reviews, 78(1), 227-245 (1998).
Garcia, Maria L. et al., Advances in Pharmacology, 39, 425-471 (1997).
Atwal, Karnail S., Medicinal Research Reviews, 12(6), 569-591 (1992).
Malmgren, A. et al., The Journal of Urology, 142, 1134-1138 (1989).
Malmgren, A. et al., The Journal of Urology, 143, 828-834 (1990).
Bonev, Adrian et al., Am. J. Physiol., 264, C1190-C1200 (1993).
Fujii, K. et al., Br. J. Pharmacol., 99, 779-785 (1990).
Gopalakrishnan, M., et al., Drug Development Research, 28, 95-127 (1993).
Grant, Thomas L. et al., The Journal of Pharmacology & Experimental Therapeutics, 259, 1158-1164 91991).
Evans, John M. et al., Progress in Medicinal Chemistry, 31, 411-446 (1994).
Badimon et al, "High Density Lipoprotein Plasma Fractions Inhibit Aortic Fatty Streaks in Cholesterol-Fed Rabbits", *Laboratory Investigation*, 60(3):455-461 (1989).
Barr et al., "Protein-lipid Relationships in Human Plasma", *American Journal of Medicine*, 11:480-493 (1951).
Beckert et al., "Imidazolidinderivate aus Oxalamidinen", *Journal of f. prakt. Chemie. Band*, 324(2):227-236 (1982).
Beckert, "Zur Umsetzung von Oxalamidinen mit Heterocumulenen der Kohlensäurereihe zu Imidazolidin-Derivaten", *Journal of f. prakt. Chemie. Band*, 332(1):65-82 (1990).
Glass et al., "Tissue Sites of Degradation of Apoprotein A-I in the Rat", *The Journal of Biological Chemistry*, 258(11):7161-7167 (1983).
Glomset, "The Plasma Lecithin: Cholesterol Acyltransferase Reaction", *Journal of Lipid Research*, 9:155-167 (1968).
Gofman et al., "Ischemic Heart Disease, Atherosclerosis, and Longevity", *Circulation*, 34:679-697 (1966).
Gordon et al., "High-Density Lipoprotein Cholesterol and Cardiovascular Disease", *Circulation*, 79:8-15 (1989).
Grow et al., "Interchange of Apoprotein Components between the Human Plasma High Density Lipoprotein Subclasses $HDL_2$ and $HDL_3$ in Vitro", *The Journal of Biological Chemistry*, 253(22):8034-8041 (1978).

(Continued)

*Primary Examiner*—Patricia L. Morris
(74) *Attorney, Agent, or Firm*—Fish & Richardson P.C.

(57) ABSTRACT

Compounds of Formula I are provided:

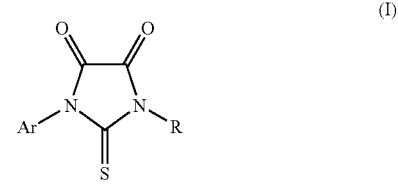

(I)

wherein:
R is lower alkyl or branched lower alkyl; and
Ar is phenyl, phenyl substituted with one or more of halogen, lower alkyl, lower alkoxy, lower alkylthio, lower alkylamino, cyano, or perfluoroalkoxy, or a heteroaromatic moiety; and pharmaceutically acceptable salts thereof.

16 Claims, No Drawings

OTHER PUBLICATIONS

Kieft et al., "Rapid on-line determination of cholesterol distribution among plasma lipoproteins after high-performance gel filtration chromatography", *Journal of Lipid Research*, 32:859-866 (1991).

Lagocki et al., "*In Vitro* Modulation of the Apolipoprotein Composition of High Density Lipoprotein", *The Journal of Biological Chemistry*, 255(8):3701-3706 (1980).

Mackinnon et al., "Metabolism of High Density Lipoproteins by the Perfused Rabbit Liver", *The Journal of Biological Chemistry*, 261(6):2548-2552 (1986).

Miller et al., "Plasma-High-Density-Lipoprotein Concentration and Development of ISCH/EMIC Heart-Disease", *The Lancet*, 1:16-19 (1975).

Miller et al., "Relation of Angiographically Defined Coronary Artery Disease to Plasma Lipoprotein Subfractions and Apolipoproteins", *British Medical Journal*, 282:1741-1744 (1981).

Picardo et al., "Partially Reassembled High Density Lipoproteins", *Arteriosclerosis*, 6(4):434-441 (1986).

Schaefer et al., "Transfer of human lymph chylomicron constituents to other lipoprotein density fractions during in vitro lipolysis", *Journal of Lipid Research*, 23:1259-1273 (1982).

Stampfer et al, "A Prospective Study of Cholesterol, Apolipoproteins, and the Risk of Myocardial Infarction", *The New England Journal of Medicine*, 325(6):373-381 (1991).

Zankowska-Jasinska et al., "1,3-Disubstituted 2-Thioxo-4,5-Imidazolidinediones and 2,4,5-Imidazolidinetriones and Their Anticonvulsant Activity", *Pol. J. Pharmacol. Pharm.*, 42:59-68 (1990).

\* cited by examiner

1,3-DISUBSTITUTED-2-THIOXO-IMIDAZOLIDINE-4,5-DIONES AS POTASSIUM CHANNEL OPENERS

FIELD OF THE INVENTION

This application claims priority from copending provisional application Ser. No. 60/340,921, filed Oct. 30, 2001, the entire disclosure of which is hereby incorporated by reference.

The present invention relates to novel 1,3-disubstituted derivatives of 2-thioxo-imidazolidine-4,5-diones and to their use in the treatment of disorders associated with smooth muscle contraction via potassium channel modulation.

BACKGROUND OF THE INVENTION

Potassium channels play a crucial role in controlling the physiological function of excitable cells; thus modulation of these channels may provide novel mechanistic approaches to treat cell dysfunction. The structure and function of physiologically important potassium channels and relevant structure-activity relationship have been thoroughly reviewed [see, eg, Atwal, K. *Medicinal Research Reviews* 1992, 12, 569–591; Gopalakrishan, M. et al *Drug Development Research* 1993, 28, 95–127; Lawson, K. *Pharmacol. Ther.* 1996, 70, 39–63; Aguilar-Bryan, L. et al *Physiol. Rev.* 1998, 78, 227–245; Evans, J. M. et al *Progress in Medicinal Chemistry*, 31; Ellis, G. P.; Luscombe, D. K., Eds.; Elsevier Science B. V., 1994; 411–447; Garcia, M. L. et al *Adv. Pharmacol.* 1997, 39, 425–471; McDonough, S. et al *Drug Development Research* 1994, 33, 190–202]. By virtue of their ability to hyperpolarize cell membranes and prevent the influx of $Ca^{2+}$ ions through voltage-gated $Ca^{2+}$ channels, compounds having activity as potassium channel openers relax smooth muscle cells. Several potent potassium-channel openers such as pinacidil and cromakalim have been studied clinically as antihypertensive agents. It has been shown that the ATP-dependent potassium channel does exist in the bladder and that it can be activated by numerous antihypertensive potassium channel openers [see, eg, Bonev, A. D. et al *Am. J. Physiol.* 1993, 264 (cell physiol 33), C1190–C1200; Fujii, K. et al. *Br. J. Pharmacol.* 1990, 99, 779–785; Malmgren, A. et al *J. Urol.* 1990, 143, 828–834; and Grant, T. L. et al *J. Pharmacol. Exp. Thera.* 1991, 269(3) 1158–1164].

European Patent No. 718290-A1 discloses carboxyalkyl heterocyclic derivatives as aldose reductase inhibitors useful in treating diabetic complications. Among the disclosed compounds are 4,5-dioxo-1-thioxoimidazolidines of the following formula:

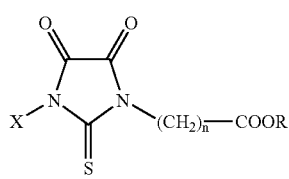

wherein:
R is hydrogen or lower alkyl of 1–3 carbon atoms;
n is an integer of 1–3; and
X is benzyl, benzothiazolylmethyl, or naphthyl methyl.

U.S. Pat. No. 5,312,919 discloses the preparation and use of merodantoin (1) as an anticancer and antiviral agent. This patent further discloses compounds of formula 2:

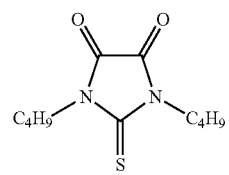

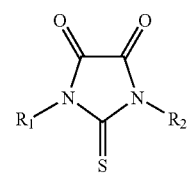

wherein:
$R_1$ and $R_2$ may be hydrogen, $C_1$–$C_6$ alkyl, or benzyl.

U.S. Pat. Nos. 4,084,001 and 4,152,453 disclose the use of compounds of the following formulas 1 and 2 as intermediates in the preparation of histamine blocking agents and as inhibitors of acid secretion respectively.

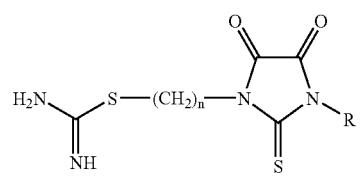

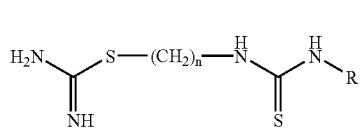

wherein:
R is alkyl; and
n is an integer of 1–6.

U.S. Pat. No. 3,461,133 discloses compounds of following formula as herbicides:

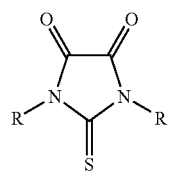

wherein:
R is alkyl of 1–12 carbon atoms, alkenyl, or alkynyl.

German Patent DE 3540919 discloses compounds of following formula as herbicidal synergists:

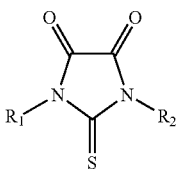

wherein:
R₁ is hydrogen, alkyl; and
R₂ is alkyl, phenyl, or phenylalkyl.

German Patent DD 154819 discloses methods for the preparation of compounds of following formula (1) from 4,5-di-imino compounds (2):

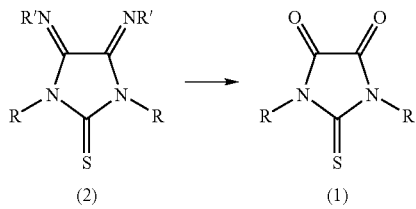

German Patent DD 219483 A1 discloses compounds of the following formula as antitubercular agents:

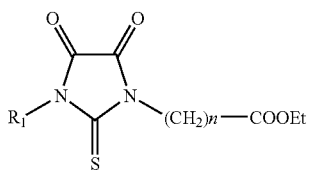

wherein:
R is aryl; and
n is an integer of 1–2.

SUMMARY OF THE INVENTION

In accordance with the present invention there are provided substituted 2-thioxo imidazolidine-4,5-dione derivatives of Formula I;

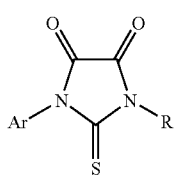

wherein:
R is lower alkyl or branched lower alkyl; and
Ar is phenyl, phenyl substituted with one or more of halogen, lower alkyl, lower alkoxy, lower alkylthio, lower alkylamino, cyano, or perfluoroalkoxy, or a heteroaromatic moiety; and pharmaceutically acceptable salts thereof.

DETAILED DESCRIPTION OF THE INVENTION

Preferably, the present compounds are those represented by Formula I:

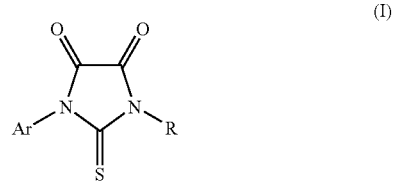

wherein:
R is lower alkyl or branched lower alkyl; and
Ar is phenyl, or phenyl substituted with one or more of halogen, lower alkyl or cyano; and pharmaceutically acceptable salts thereof.

As used herein, the terms "lower alkyl", "lower alkoxy", "lower alkylthio" and "lower alkylamino" are meant to include both straight and branched chain moieties containing 1–10 carbon atoms. The term "halogen" is meant to include fluorine, chlorine, bromine, and iodine.

Examples of "heteroaromatic moieties" useful in the present invention include substituted and unsubstituted pyridyl, thiophenes, benzothiophenes, benzofurans, quinolines, isoquinolines, indoles, oxazoles, and benzoxazoles.

The pharmaceutically acceptable salts of the present compounds include those derived from organic and inorganic acids such as acetic, lactic, citric, tartaric, succinic, fumaric, maleic, malonic, mandelic, malic, hydrochloric, hydrobromic, phosphoric, nitric, sulfuric, methanesulfonic, toluenesulfonic, and similarly acceptable acids.

It is understood that the definition of the compounds of formula (I), when R contains asymmetric carbons, encompasses all possible stereoisomers and mixtures thereof which possess the activity discussed below. In particular, it encompasses racemic modifications and any optical isomers which possess the indicated activity. Optical isomers may be obtained in pure form by standard separation techniques or enantiomer specific synthesis. It is understood that this invention encompasses all crystalline forms of compounds of formula (I). The pharmaceutically acceptable salts of the basic compounds of this invention are those derived from such organic and inorganic acids as: lactic, citric, acetic, tartaric, succinic, maleic, malonic, hydrochloric, hydrobromic, phosphoric, nitric, sulfuric, methanesulfonic, and similarly known acceptable acids. Where R contains a carboxyl group, salts of the compounds of this invention may be formed with bases such as alkali metals (Na, K, Li) or the alkaline earth metals (Ca or Mg).

The most preferred compounds of this invention are:
4-[4,5-Dioxo-2-thioxo-3-(1,2,2-trimethyl-propyl)-imidazolidin-1-yl]-benzonitrile;
4-[3-(2,2-Dimethyl-propyl)-4,5-dioxo-2-thioxo-imidazolidin-1-yl]-benzonitrile;
4-[3-(1,1-Dimethyl-propyl)-4,5-dioxo-2-thioxo-imidazolidin-1-yl]-benzonitrile;
4-(3-tert-Butyl-4,5-dioxo-2-thioxo-imidazolidin-1-yl)-benzonitrile;
4-[3-(1,1-Dimethyl-propyl)-4,5-dioxo-2-thioxo-imidazolidin-1-yl]-3-ethyl-benzonitrile;

4-[4,5-Dioxo-2-thioxo-3-((1R)-1,2,2-trimethyl-propyl)-imi-
   dazolidin-1-yl]-benzonitrile 3-[4,5-Dioxo-2-thioxo-3-(1,
   2,2-trimethyl-propyl)-imidazolidin-1-yl]-benzonitrile;
1-(4-Bromo-phenyl)-2-thioxo-3-(1,2,2-trimethyl-propyl)-
   imidazolidine-4,5-dione;
1-(4-Dimethylamino-phenyl)-3-(2,2-dimethyl-propyl)-2-
   thioxo-imidazolidine-4,5-dione hydrochloride;
1-(2,2-Dimethyl-propyl)-3-pyridin-3-yl-2-thioxo-imidazoli-
   dine-4,5-dione;
1-(2,4-Difluoro-phenyl)-2-thioxo-3-(1,2,2-trimethyl-pro-
   pyl)-imidazolidine-4,5-dione;
1-(4-Chloro-phenyl)-2-thioxo-3-(1,2,2-trimethyl-propyl)-
   imidazolidine-4,5-dione;
1-(2,4-Difluoro-phenyl)-3-(2,2-dimethyl-propyl)-2-thioxo-
   imidazolidine-4,5-dione;
1-(2,2-Dimethyl-propyl)-3-(4-fluoro-phenyl)-2-thioxo-imi-
   dazolidine-4,5-dion; and
1-(4-tert-Butyl-phenyl)-2-thioxo-3-(1,2,2-trimethyl-pro-
   pyl)-imidazolidine-4,5-dione.

The compounds of the invention can be readily prepared according to the following reaction scheme or a modification thereof using readily available starting materials, reagents and conventional synthetic procedures. It is also possible to make use of variants of these process steps, which in themselves are known to and well within the preparatory skill of the medicinal chemist. In the following reaction scheme $R_1$ and $R_2$ may represent, independently, halogen, lower alkyl, lower alkoxy, lower alkylthio, lower alkylamino, cyano, or perfluoroalkoxy and $R_3$ may represent lower alkyl or branched lower alkyl. Aryl and alkyl isothiocyanates may be used as starting materials.

carried out at room temperature or at reflux for 1 to 2 hours followed by solvent evaporation, and aqueous work up.

The present compounds have been found to relax smooth muscle via potassium channel modulation. They are therefore useful in the treatment of disorders associated with smooth muscle contraction, including disorders involving excessive smooth muscle contraction of the urinary tract (such as incontinence), or of the gastrointestinal tract (such as irritable bowel syndrome), asthma, and hair loss. Furthermore, the activity of the present compounds on potassium channels renders them useful for treatment of peripheral vascular disease, hypertension, congestive heart failure, stroke, anxiety, cerebral anoxia and other neurodegenerative disorders.

The present invention further provides pharmaceutical compositions which comprise an effective amount of the present compounds in combination or association with a pharmaceutically acceptable carrier. The compositions are preferably adapted for oral administration. However, they may be adapted for other modes of administration, for example, parenteral administration for patients suffering from heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. More preferred unit dosage forms contain 5 to 25 mg of the present compound. The compounds of the present invention can be administered orally at a dose range of about 0.01 to 100

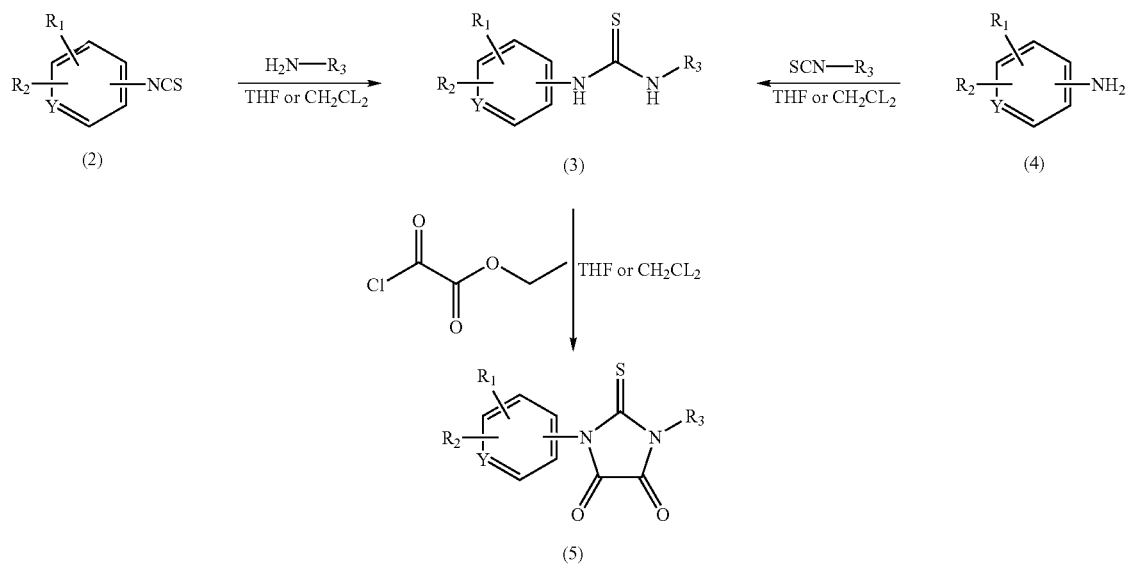

The reaction of aryl isothiocyanates (2) with primary amines in a solvent such as water, diethyl ether, THF or dichloromethane conducted for a period of 1 to 24 hours followed by evaporation of the solvent afforded the requisite thioureas (3). Alternatively, the same thioureas may be prepared by reacting an alkyl isothiocyanate with an appropriately substituted aniline (4) to give thioureas (3). Reaction of these intermediates with ethyl chlorooxoacetate or oxalyl chloride in a solvent such as dichloromethane afforded the target molecules (5). The reactions can be mg/kg or preferably at a dose range of 0.1 to 10 mg/kg. Such compositions may be administered from 1 to 6 times a day, preferably from 1 to 4 times a day.

The compositions of the invention may be formulated with conventional excipients, such as a filler, a disintegrating agent, a binder, a lubricant, a flavoring agent and the like.

The present invention is further directed to a method of treating smooth muscle disorders in mammals including man, which comprises administering to the afflicted mammal an effective amount of a compound or a pharmaceutical composition of the invention.

The following examples are presented to illustrate rather than limit the methods for production of representative compounds of the invention.

EXAMPLE 1

4-[4,5-Dioxo-2-thioxo-3-(1,2,2-trimethyl-propyl)-imidazolidin-1-yl]-benzonitrile To a solution of 4-cyanophenyl isothiocyanate (2.00 g, 12.5 mmol) in THF (50 mL) at room temperature was added a solution of (±) 3,3-dimethyl-2-aminobutane (2.00 mL, 14.5 mmol) in THF (12 mL) and the reaction was stirred overnight at room temperature. The mixture was concentrated in vacuo and the resulting residue was triturated with diethyl ether and filtered to afford 3.12 g (96%) of 1-(4-cyanophenyl)-3-(1,2,2-trimethyl-propyl)-thiourea as a white solid which was used without further purification.

Ethyl chlorooxoacetate (5.60 mL, 50.0 mmol) was added to a stirring solution of the above thiourea (6.54 g, 25.0 mmol) in dichloromethane (170 mL) and the resulting mixture was stirred overnight at room temperature. Concentration, trituration of the residue with diethyl ether, and filtration afforded 5.77 g (73%) of 4-[4,5-dioxo-2-thioxo-3-(1,2,2-trimethyl-propyl)-imidazolidin-1-yl]-benzonitrile as a yellow solid: mp 219.6–219.9° C.; $^1$H NMR (DMSO-d$_6$): δ 8.03 (d, 2H), 7.60 (d, 2H), 4.82 (q, 1H), 1.47 (d, 3H), 1.00 (s, 9H); IR (KBr): 3505, 2970, 2230, 1765, 1600 cm$^{-1}$; MS (m/z) 315 (M$^+$).

Elemental Analysis for C$_{16}$H$_{17}$N$_3$O$_2$S Calcd: C, 60.93; H, 5.43; N, 13.32. Found: C, 60.91; H, 5.42; N, 13.17.

EXAMPLE 2

4-[3-(2,2-Dimethyl-propyl)-4,5-dioxo-2-thioxo-imidazolidin-1-yl]-benzonitrile

To a solution of 4-cyanophenyl isothiocyanate (1.00 g, 6.24 mmol) in THF (30 mL) at room temperature was added a solution of neopentylamine (1.09 g, 12.5 mmol) in THF (30 mL) and the reaction was stirred overnight at room temperature. The mixture was concentrated in vacuo and the resulting residue was triturated with diethyl ether and filtered to afford 1.43 g (96%) of 1-(4-cyanophenyl)-3-(2,2-diimethyl-propyl)-thiourea as a white solid which was used without further purification.

Ethyl chlorooxoacetate (1.33 mL, 11.9 mmol) was added dropwise to a stirring solution of 1-(4-cyanophenyl)-3-(2,2-diimethyl-propyl)-thiourea (1.473 g, 5.95 mmol) in dichloromethane (30 mL) and the resulting mixture was heated to reflux for 45 minutes. The mixture was cooled and concentrated to afford a residue which was triturated with diethyl ether. Filtration afforded 1.43 g (80%) of 4-[3-(2,2-dimethyl-propyl)-4,5-dioxo-2-thioxo-imidazolidin-1-yl]-benzonitrile as a yellow solid: mp 128–129° C.; $^1$H NMR (DMSO-d$_6$): δ 8.04 (d, 2H), 7.61 (d, 2H), 3.76 (s, 2H), 0.993 (s, 9H); IR (KBr) 3500, 2950, 2220, 1760, 1610 cm$^{-1}$; MS (m/z) 301 (M$^+$).

Elemental Analysis for C$_{15}$H$_{15}$N$_3$O$_2$S.0.2H$_2$O Calcd: C, 59.08; H, 5.09; N, 13.78. Found: C, 59.17; H, 4.94; N, 13.72.

EXAMPLE 3

4-[3-(1,1-Dimethyl-propyl)-4,5-dioxo-2-thioxo-imidazolidin-1-yl]-benzonitrile

To a solution of 4-cyanophenyl isothiocyanate (1.00 g, 6.24 mmol) in THF (25 mL) at room temperature was added a solution of tert-amylamine (1.46 mL, 12.5 mmol) and the reaction was stirred overnight at room temperature. The mixture was concentrated in vacuo and the resulting residue was triturated with diethyl ether and filtered to afford 1.20 g (78%) of 1-(4-cyanophenyl)-3-(1,1-diimethyl-propyl)-thiourea as a white solid which was used without further purification.

Ethyl chlorooxoacetate (0.73 mL, 6.50 mmol) was added dropwise to a stirring solution of 1-(4-cyanophenyl)-3-(1,1-diimethyl-propyl)-thiourea (0.802 g, 3.25 mmol) in dichloromethane (40 mL) and the resulting mixture was stirred at room temperature overnight. The mixture was concentrated to afford a residue which was purified by flash column chromatography (10% ethyl acetate/hexanes) to afford 0.60 g (61%) of 4-[3-(1,1-dimethyl-propyl)-4,5-dioxo-2-thioxo-imidazolidin-1-yl]-benzonitrile as a yellow solid: mp 173.1–174.3° C.; $^1$H NMR (DMSO-d$_6$): δ 8.02 (d, 2H), 7.55 (d, 2H), 2.20 (q, 2H), 1.75 (s, 6H), 0.92 (t, 3H); IR (KBr) 3500, 2220, 1760 1610 cm$^{-1}$; MS (m/z) 302 (M+H$^+$).

Elemental Analysis for C$_{15}$H$_{15}$N$_3$O$_2$S Calcd: C, 59.78; H, 5.02; N, 13.94. Found: C, 59.65; H, 4.99; N, 13.48.

EXAMPLE 4

4-(3-tert-Butyl-4,5-dioxo-2-thioxo-imidazolidin-1-yl)-benzonitrile

To a solution of 4-cyanophenyl isothiocyanate (1.00 g, 6.24 mmol) in THF (25 mL) at room temperature was added a solution of tert-butylamine (1.31 mL, 12.5 mmol) and the reaction was stirred at room temperature for 6 hours. The mixture was concentrated in vacuo and the resulting residue was triturated with diethyl ether and filtered to afford 1.37 g (94%) of 1-(4-cyanophenyl)-3-(tert-butyl)-thiourea as a white solid which was used without further purification.

Ethyl chlorooxoacetate (1.15 mL, 10.29 mmol) was added dropwise to a stirring solution of 1-(4-cyanophenyl)-3-(tert-butyl)-thiourea (0.802 g, 3.25 mmol) in dichloromethane (40 mL) and the resulting mixture was stirred at room temperature overnight. The mixture was concentrated to afford a residue which was purified by flash column chromatography (50% ethyl acetate/hexanes) to afford 0.48 g (32%) of 4-[3-(tert-butyl)-4,5-dioxo-2-thioxo-imidazolidin-1-yl]-benzonitrile as a yellow solid: mp 200.4–201.3° C.; $^1$H NMR (DMSO-d$_6$): δ 8.00 (d, 2H), 7.52 (d, 2H), 2.20 (q, 2H), 1.79 (s, 9H); IR (KBr) 3500, 2220, 1760 cm$^{-1}$; MS (m/z) 287 (M$^+$).

Elemental Analysis for C$_{14}$H$_{13}$N$_3$O$_2$S Calcd: C, 58.52; H, 4.56; N, 14.62. Found: C, 58.55; H, 4.57; N, 14.50.

EXAMPLE 5

4-[3-(1,1-Dimethyl-propyl)-4,5-dioxo-2-thioxo-imidazolidin-1-yl]-3-ethyl-benzonitrile To a solution of 3-ethyl-4-aminobenzonitrile (1.35 g, 9.29 mmol) in DMF (10 mL) at room temperature was added sodium hydride (0.28 g, 80%, 9.29 mmol). The mixture was heated to 70° C. for 40 minutes and was then cooled to room temperature. A solution of tert-amyl isothiocyanate (1.0 g, 7.74 mmol) in DMF (1 mL) was added by syringe and the reaction was stirred at 70° C. overnight. The cooled reaction mixture was diluted with 2N HCl and water and the mixture was extracted with ethyl acetate. The organic phase was dried and concentrated to afford an oil. The crude product was taken up in a minimal amount of diethyl ether and the solution was made turbid by adding petroleum ether. Sonication resulted in the formation of a precipitate which was collected by filtration to afford 1.2 g (56%) of 1-(2-ethyl-4-cyanophenyl)-3-(1,1-dimethyl-propyl)-thiourea as an off-white solid which was used without further purification.

Ethyl chlorooxoacetate (0.82 mL, 7.3 mmol) was added dropwise to a stirring solution of 1-(2-ethyl-4-cyanophenyl)-3-(1,1-dimethyl-propyl)-thiourea (1.0 g, 3.65 mmol) in dichloromethane (30 mL) and the resulting mixture was stirred at room temperature overnight. The mixture was concentrated to afford a residue which was triturated with diethyl ether and hexanes to afford 0.71 g (59%) of 4-[3-(1,1-dimethyl-propyl)-4,5-dioxo-2-thioxo-imidazolidin-1-yl]-3-ethyl-benzonitrile as a yellow solid: mp 172.8–173.3° C.; $^1$H NMR (DMSO-$d_6$): δ 7.92 (s, 1H), 7.80 (d, 1H), 7.52 (d, 1H), 2.50 (m, 2H), 2.19 (m, 2H), 1.76 (2s, 6H), 1.08 (t, 3H), 0.85 (t, 3H); IR (KBr) 3400, 2950, 2260, 1775 cm$^{-1}$; MS (m/z) 329 (M$^+$).

Elemental Analysis for $C_{17}H_{19}N_3O_2S$ Calcd: C, 61.98; H, 5.81; N, 12.76. Found: C, 61.21; H, 5.67; N, 12.56.

EXAMPLE 6

4-[4,5-Dioxo-2-thioxo-3-((1R)-1,2,2-trimethyl-propyl)-imidazolidin-1-yl]-benzonitrile The compound was prepared in a similar manner to that reported for the racemic compound in Example 1 utilizing (R)-(+) 3,3-dimethyl-2-aminobutane (*J. Med. Chem.*, 1992, 35, 2327–2340) instead of racemic 3,3-dimethyl-2-aminobutane. Yield for step one: 91%. Yield for step two: 53%. The title compound was isolated as a yellow solid: mp 197.6–197.8° C.; [α]$^{25}$D=–102.93 (CH$_2$CL$_2$); $^1$H NMR (DMSO-$d_6$): δ 8.03 (d, 2H), 7.60 (d, 2H), 4.82 (q, 1H), 1.47 (d, 3H), 1.00 (s, 9H). IR (KBr): 3500, 2970, 2230, 1765, 1600 cm$^{-1}$; MS (m/z) 315 (M$^+$).

Elemental Analysis for $C_{16}H_{17}N_3O_2S$ Calcd: C, 60.93; H, 5.43; N, 13.32. Found: C, 60.04; H, 5.18; N, 13.23.

EXAMPLE 7

3-[4,5-Dioxo-2-thioxo-3-(1,2,2-trimethyl-propyl)-imidazolidin-1-yl]-benzonitrile To a solution of 3-cyanophenyl isothiocyanate (1.00 g, 6.24 mmol) in THF (25 mL) at room temperature was added (±) 3,3-dimethyl-2-aminobutane (1.08 mL, 9.36 mmol) and the reaction was stirred overnight at room temperature. The mixture was concentrated in vacuo and the resulting residue was triturated with diethyl ether and filtered to afford 1.2 g (78%) of 1-(3-cyanophenyl)-3-(1,2,2-trimethyl-propyl)-thiourea as a white solid which was used without further purification.

Ethyl chlorooxoacetate (1.03 mL, 9.17 mmol) was added to a stirring solution of the above thiourea (1.19 g, 4.59 mmol) in dichloromethane (30 mL) and the resulting mixture was stirred overnight at room temperature. Concentration, trituration of the residue with diethyl ether, and filtration afforded 1.167 g (81%) of 3-[4,5-dioxo-2-thioxo-3-(1,2,2-trimethyl-propyl)-imidazolidin-1-yl]-benzonitrile as a yellow solid: mp 168.1–168.7° C.; $^1$H NMR (DMSO-$d_6$): δ8.00 (d, 1H), 7.84 (s, 1H), 7.75 (m, 2H), 4.83 (q, 1H), 1.47 (d, 3H), 1.01 (s, 9H); IR (KBr): 3500, 2970, 2230, 1765, 1600 cm$^{-1}$; MS (m/z) 315 (M$^+$).

Elemental Analysis for $C_{16}H_{17}N_3O_2S$ Calcd: C, 60.93; H, 5.43; N, 13.32. Found: C, 60.73; H, 5.31; N, 13.14.

EXAMPLE 8

1-(4-Bromo-phenyl)-2-thioxo-3-(1,2,2-trimethyl-propyl)-imidazolidine-4,5-dione

To a solution of 4-bromophenyl isothiocyanate (1.50 g, 7.01 mmol) in THF (30 mL) at room temperature was added (±) 3,3-dimethyl-2-aminobutane (1.41 mL, 10.5 mmol) and the reaction was stirred overnight at room temperature. The mixture was concentrated in vacuo and the resulting residue was triturated with diethyl ether and filtered to afford 1.76 g (80%) of 1-(4-bromophenyl)-3-(1,2,2-trimethyl-propyl)-thiourea as a white solid which was used without further purification.

Ethyl chlorooxoacetate (0.496 mL, 4.44 mmol) was added to a stirring solution of the above thiourea (0.70 g, 2.22 mmol) in dichloromethane (15 mL) and the resulting mixture was stirred overnight at room temperature. Concentration, trituration of the residue with diethyl ether, and recrystallization from boiling methanol afforded 0.647 g (79%) of 1-(4-bromo-phenyl)-2-thioxo-3-(1,2,2-trimethyl-propyl)-imidazolidine-4,5-dione as a yellow solid: mp 207.1–207.9° C.; $^1$H NMR (DMSO-$d_6$): δ 7.74 (d, 1H), 7.32 (d, 2H), 4.81 (q, 1H), 1.48 (d, 3H), 0.99 (s, 9H); IR (KBr): 3500, 2970, 2230, 1770, 1500 cm$^{-1}$; MS (m/z) 368 (M$^+$).

Elemental Analysis for $C_{15}H_{17}BrN_2O_2S$ Calcd: C, 48.79; H, 4.64; N, 7.59. Found: C, 48.18; H, 4.42; N, 7.47.

EXAMPLE 9

1-(4-Dimethylamino-phenyl)-3-(2,2-dimethyl-propyl)-2-thioxo-imidazolidine-4,5-dione Hydrochloride To a solution of 4-dimethylaminophenyl isothiocyanate (4.5 g, 25 mmol) in diethyl ether (100 mL) at room temperature was added a solution of 2,2-dimethyl-1-propanamine (2.94 mL, 25 mmol) and the reaction was stirred at room temperature for 3 hours. The precipitated solid was collected by filtration and dried to afford 5.7 g (85%) of N-[4-(dimethylamino)phenyl]-N'-(2,2-dimethylpropyl)-thiourea, as a white solid: mp 174–176° C.; $^1$H NMR (DMSO-$d_6$): δ 9.17 (br s, 1H), 7.13 (d, 2H), 7.10 (br s, 1H), 6.68 (d, 2H), 3.33 (d, 2H), 2.86 (s, 6H), and 0.87 ppm (s, 9H); IR (KBr) 3400, 3160, 1600, 1550 cm$^{-1}$; MS (m/z) 265 (M$^+$).

Elemental Analysis for $C_{14}H_{23}N_3S$ Calcd: C, 63.35; H, 8.73; N, 15.83. Found: C, 63.35; H, 8.48; N, 15.86.

Ethyl chlorooxoacetate (3.4 mL, 30 mmol) was added dropwise to a stirring solution of N-[4-(dimethylamino)phenyl]-N'-(2,2-dimethylpropyl)-thiourea (3.98 g, 15 mmol) in dichloromethane (100 mL) and the resulting mixture was stirred at room temperature overnight. The solvent was evaporated. The residue was treated with ether (100 mL) and the mixture was stirred for one hour. The solid was collected by filtration, washed with fresh ether and dried to give 5.3 g (100%) of the title compound: mp. 244–246° C.; $^1$H NMR (DMSO-$d_6$): δ7.28 (d, 2H), 7.20 (br s, 2H), 3.74 (s, 2H), 3.02 (s, 6H), and 0.98 ppm (s, 9H); IR (KBr) 3640, 3080, 2350, 1775 cm$^{-1}$; MS (m/z) 319 (M$^+$).

Elemental Analysis for $C_{16}H_{21}N_3O_2S \cdot HCl$ Calcd: C, 54.00; H, 6.23; N, 11.81; Cl, 9.96. Found: C, 53.96; H, 6.11; N, 11.61; Cl, 9.77.

EXAMPLE 10

1-(2,4-Difluoro-phenyl)-2-thioxo-3-(1,2,2-trimethyl-propyl)-imidazolidine-4,5-dione To a solution of 2,4-difluoro-phenyl isothiocyanate (1.00 g, 5.84 mmol) in dichloromethane (20 mL) at room temperature was added (±) 3,3-dimethyl-2-aminobutane (1.02 mL, 7.6 mmol) and the reaction was stirred overnight at room temperature. The mixture was concentrated in vacuo and the resulting residue was triturated with diethyl ether and filtered to afford 1.34 g (84%) of 1-(2,4-difluoro-phenyl)-3-(1,2,2-trimethyl-propyl)-thiourea as a white solid which was used without further purification.

Ethyl chlorooxoacetate (0.53 mL, 4.77 mmol) was added to a stirring solution of the above thiourea (1.00 g, 3.67 mmol) in dichloromethane (15 mL) and the resulting mixture was stirred overnight at room temperature. Concentration, trituration of the residue with diethyl ether, and recrystallization from boiling methanol afforded 0.75 g (62%) of 1-(2,4-difluoro-phenyl)-2-thioxo-3-(1,2,2-trimethyl-propyl)-imidazolidine-4,5-dione as a yellow solid: mp 155.2–156.0° C.; $^1$H NMR (DMSO-$d_6$): δ 7.55 (m, 2H), 7.30 (m, 1H), 4.80 (m, 1H), 1.51 (d, 3H), 0.99 (s, 9H); IR (KBr): 3550, 2970, 2230, 1770 cm$^1$; MS (m/z) 326 (M$^+$).

Elemental Analysis for $C_{15}H_{16}F_2N_2O_2S$ Calcd: C, 55.20; H, 4.94; N, 8.58. Found: C, 54.95; H, 4.85; N, 8.56.

EXAMPLE 11

1-(2,4-Difluoro-phenyl)-3-(2,2-dimethyl-propyl)-2-thioxo-imidazolidine-4,5-dione To a solution of 2,4-difluoro-phenyl isothiocyanate (1.00 g, 5.84 mmol) in dichloromethane (20 mL) at room temperature was added neopentylamine (0.90 mL, 7.6 mmol) and the reaction was stirred overnight at room temperature. The mixture was concentrated in vacuo and the resulting residue was triturated with diethyl ether and filtered to afford 1.28 g (85%) of 1-(2,4-difluoro-phenyl)-3-(2,2-dimethyl-propyl)-thiourea as a white solid which was used without further purification.

Ethyl chlorooxoacetate (0.57 mL, 5.03 mmol) was added to a stirring solution of the above thiourea (1.00 g, 3.87 mmol) in dichloromethane (15 mL) and the resulting mixture was stirred overnight at room temperature. Concentration, trituration of the residue with diethyl ether, and recrystallization from boiling methanol afforded 0.66 g (55%) of 1-(2,4-difluoro-phenyl)-3-(2,2-dimethyl-propyl)-2-thioxo-imidazolidine-4,5-dione as a yellow solid: mp 156.2–156.9° C.; $^1$H NMR (DMSO-$d_6$): δ 7.55 (m, 2H), 7.30 (m, 1H), 3.76 (m, 2H), 0.95 (s, 9H); IR (KBr): 3510 2920, 2230, 1775 cm$^1$; MS (m/z) 312 (M$^+$).

Elemental Analysis for $C_{14}H_{14}F_2N_2O_2S$ Calcd: C, 53.84; H, 4.52; N, 8.97. Found: C, 53.59; H, 4.43; N, 8.92.

EXAMPLE 12

1-(4-Chloro-phenyl)-2-thioxo-3-(1,2,2-trimethyl-propyl)-imidazolidine-4,5-dione To a solution of 4-chloro-phenyl isothiocyanate (1.00 g, 5.90 mmol) in THF (20 mL) at room temperature was added (±) 3,3-dimethyl-2-aminobutane (1.03 mL, 7.66 mmol) and the reaction was stirred overnight at room temperature. The mixture was concentrated in vacuo and the resulting residue was triturated with diethyl ether and filtered to afford 1.29 g (81%) of 1-(4-chloro-phenyl)-3-(1,2,2-trimethylpropyl)-thiourea as a white solid which was used without further purification.

Ethyl chlorooxoacetate (0.62 mL, 5.60 mmol) was added to a stirring solution of the above thiourea (1.00 g, 3.72 mmol) in dichloromethane (15 mL) and the resulting mixture was stirred overnight at room temperature. Concentration, trituration of the residue with diethyl ether, and recrystallization from boiling methanol afforded 0.72 g (60%) of 1-(4-chloro-phenyl)-2-thioxo-3-(1,2,2-trimethyl-propyl)-imidazolidine-4,5-dione as a yellow solid: mp 198.8–199.5° C.; $^1$H NMR (DMSO-$d_6$): δ 7.61 (d, 2H), 7.40 (d, 2H), 4.82 (q, 1H), 1.45 (d, 3H), 0.98 (s, 9H); IR (KBr): 3500, 2920, 1775 cm$^1$; MS (m/z) 324 (M$^+$).

Elemental Analysis for $C_{15}H_{17}ClN_2O_2S$ Calcd: C, 55.46; H, 5.28; N, 8.62. Found: C, 55.34; H, 5.26; N, 8.58.

EXAMPLE 13

1-(4-tert-Butyl-phenyl)-2-thioxo-3-(1,2,2-trimethyl-propyl)-imidazolidine-4,5-dione To a solution of 4-tert-butyl-isothiocyanate (1.00 g, 5.23 mmol) in THF (20 mL) at room temperature was added (±) 3,3-dimethyl-2-aminobutane (0.91 mL, 6.7 mmol) and the reaction was stirred overnight at room temperature. The mixture was concentrated in vacuo and the resulting residue was triturated with diethyl ether and filtered to afford 1.05 g (69%) of 1-(4-tert-butyl-phenyl)-3-(1,2,2-trimethylpropyl)-thiourea as a white solid which was used without further purification.

Ethyl chlorooxoacetate (0.46 mL, 4.10 mmol) was added to a stirring solution of the above thiourea (0.80 g, 2.74 mmol) in dichloromethane (15 mL) and the resulting mixture was stirred overnight at room temperature. Concentration, trituration of the residue with diethyl ether, and recrystallization from boiling methanol afforded 0.61 g (64%) of 1-(4-tert-butyl-phenyl)-2-thioxo-3-(1,2,2-trimethyl-propyl)-imidazolidine-4,5-dione as a yellow solid: mp 208.9–209.5° C.; $^1$H NMR (DMSO-$d_6$): δ 7.52 (d, 2H), 7.40 (d, 2H), 4.85 (q, 1H), 1.48 (d, 3H), 1.30 (s, 9H), 1.00 (s, 9H); IR (KBr): 3505, 2930, 1780 cm$^1$; MS (m/z) 346 (M$^+$).

Elemental Analysis for $C_{19}H_{26}N_2O_2S$ Calcd: C, 65.86; H, 7.56; N, 8.09. Found: C, 65.85; H, 7.52; N, 8.04.

EXAMPLE 14

1-(2,2-Dimethyl-propyl)-3-(4-fluoro-phenyl)-2-thioxo-imidazolidine-4,5-dione To a solution of 4-fluoro-phenylisothiocyanate (1.00 g, 6.53 mmol) in dichloromethane (20 mL) at room temperature was added neopentylamine (1.00 mL, 8.5 mmol) and the reaction was stirred overnight at room temperature. The mixture was concentrated in vacuo and the resulting residue was triturated with diethyl ether and filtered to afford 1.42 g (90%) of 1-(4-fluoro-phenyl)-3-(2,2-dimethylpropyl)-thiourea as a white solid which was used without further purification.

Ethyl chlorooxoacetate (0.60 mL, 5.41 mmol) was added to a stirring solution of the above thiourea (1.00 g, 4.16 mmol) in dichloromethane (20 mL) and the resulting mixture was stirred overnight at room temperature. Concentration, trituration of the residue with diethyl ether, and recrystallization from boiling methanol afforded 0.77 g (62%) 1-(2,2-dimethyl-propyl)-3-(4-fluoro-phenyl)-2-thioxo-imidazolidine-4,5-dione as an orange-yellow solid: mp 165.2–166.3° C.; $^1$H NMR (DMSO-$d_6$): δ 7.40 (m, 4H), 3.73 (s, 2H), 0.98 (s, 9H); IR (KBr): 3500, 2980, 1770 cm$^1$; MS (m/z) 294 (M$^+$).

Elemental Analysis for $C_{14}H_{15}FN_2O_2S$ Calcd: C, 57.13; H, 5.14; N, 9.52. Found: C, 57.07; H, 5.04; N, 9.48.

EXAMPLE 15

1-(2,2-Dimethyl-propyl)-3-pyridin-3-yl-2-thioxo-imidazolidine-4,5-dione

To a solution of 3-pyridyl-isothiocyanate (1.50 mL, 13.3 mmol) in THF (30 mL) at room temperature was added neopentylamine (2.35 mL, 19.8 mmol) and the reaction was stirred overnight at room temperature. The mixture was concentrated in vacuo and the resulting residue was triturated with diethyl ether and filtered to afford 2.64 g (89%) of 1-(3-pyridyl)-3-(2,2-dimethylpropyl)-thiourea as an off-white solid which was used without further purification.

Ethyl chlorooxoacetate (0.33 mL, 2.90 mmol) was added to a stirring solution of the above thiourea (0.50 g, 2.24 mmol) and $K_2CO_3$ (0.31 g) in dichloromethane (15 mL) and the resulting mixture was stirred overnight at room temperature. Concentration, trituration of the residue with diethyl ether, and recrystallization from boiling methanol afforded 0.50 g (81%) 1-(2,2-dimethyl-propyl)-3-pyridin-3-yl-2-thioxo-imidazolidine-4,5-dione as a yellow solid: mp 111.4–112.8° C.; IR (KBr): 3500, 2980, 1770 $cm^1$; MS (m/z) 378 $(M+H^+)$.

Elemental Analysis for $C_{13}H_{15}N_3O_2S$ Calcd: C, 56.30; H, 5.45; N, 15.15. Found: C, 56.63; H, 5.67; N, 15.18.

The smooth muscle relaxing activity of the compounds of the present invention was demonstrated in accordance with standard pharmaceutically accepted test procedures with representative compounds as follows:

Sprague-Dawley rats (150–200 g) were rendered unconscious by $CO_2$ asphyxiation and then euthanized by cervical dislocation. The bladder was removed into warm (37 deg.C.) physiological salt solution (PSS) of the following composition (mM): NaCl, 118.4; KCl, 4.7; $CaCl_2$, 2.5; $MgSO_4$, 4.7; $H_2O$, 1.2; $NaHCO_3$, 24.9; $KH_2PO_4$, 1.2; glucose, 11.1; EDTA, 0.023; gassed with 95% $O_2$; 2/5% $CO_2$; pH 7.4. The bladder was opened and then cut into strips 1–2 mm in width and 7–10 mm in length. The strips are subsequently suspended in a 10 mL tissue bath under an initial resting tension of 1.5 g. The strips were held in place by two surgical clips one of which is attached to a fixed hook while the other is attached to an isometric force transducer. The preparations, which usually exhibit small spontaneous contractions, were allowed to recover for a period of 1 hour prior to a challenge with 0.1 uM carbachol. The carbachol was then washed out and the tissue allowed to relax to its resting level of activity. Following a further 30 minute period of recovery an additional 15 mM KCl were introduced into the tissue bath. This increase in KCl concentration resulted in a large increase in the amplitude of spontaneous contractions (and initiation of contractions in previously quiescent strips) superimposed upon a small increase in basal tone. Following stabilization of this enhanced level of contractile activity, incremental increases in the concentration of test compound or vehicle were introduced into the tissue bath. Contractile activity was measured for each compound or vehicle concentration during the last minute of a 30 minute challenge.

The isometric force developed by the bladder strips was measured using a concentration required to elicit 50% inhibition of pre-drug contractile activity ($IC_{50}$ concentration) and was calculated from this concentration-response curve. The maximum percentage inhibition of contractile activity evoked by a test compound was also recorded for concentrations of test compound less than or equal to 30 μM.

The results of this study are shown in Table I:

TABLE I

Inhibition of Contractions in Isolated Rat Bladder Strips

| Compound | n | $IC_{50}$—μM or *% Inhibition @ 30 μM |
|---|---|---|
| Example 1 | 2 | 3.3 ± 0.08 |
| Example 2 | 2 | 3.4 ± 0.8 |
| Example 3 | 2 | 25.7 ± 3.7 |
| Example 4 | 2 | 30.0 ± 5.0 |
| Example 5 | 2 | 28.9 ± 2.6 |
| Example 6 | 4 | 4.2 ± 1.4 |
| Example 7 | 2 | *I = 29.2 ± 5.4% |
| Example 8 | 1 | 27.2 |
|  | 1 | *I = 22.4% |
| Example 9 | 3 | *I = 33.2 ± 1.7% |
| Example 10 | 2 | *I = 23.1 ± 4.3% |
| Example 11 | 2 | *I = 30.6 ± 4.7% |
| Example 12 | 2 | *I = 24.3 ± 7.7% |
| Example 13 | 2 | *I = 18.3 ± 6.6% |
| Example 14 | 2 | *I = 15.0 ± 7.8% |
| Example 15 | 2 | 3.6 ± 0.8 |

*Percent inhibition at 30 μM

In addition, the ability of the present compounds to inhibit the hyperactivity of hypertrophied bladder (detrusor) smooth muscle in conscious female rats with hypertrophied bladders and thereby alleviate urinary incontinence in rats was tested according to the protocol described by Malmgrem (A. Malmgren, K. E. Andersson, C. Sjogren, P. O. Andersson, Effects of Pinacidil and Cromakalim (BRL 34915) on Bladder Function in Rats with Detrusor Instability, *J. Urol.* 142:1134, 1989.):

Female Sprague-Dawley rats, ranging in weight from 190–210 g were used. Up to 25 animals were prepared each time. After development of bladder hypertrophy 4–8 animals were used per test.

The compounds were dissolved in PEG-200 and administered by gastric gavage or intraveneously in a volume of 5 ml/kg. For primary screening all drugs were administered at the arbitrary dose of 10 mg/kg p.o. to groups of 4 rats.

The animals were anesthetized with halothane. Through a midline incision the bladder and urethra were exposed and a ligature of 4-0 silk was tied around the proximal urethra in the presence of a stainless steel rod (1 mm diameter) to produce a partial occlusion. The rod was then removed. The abdominal region was closed using surgical staples and each rat received 150,000 units of bicillin C-R. The animals were allowed six weeks to develop sufficient bladder hypertrophy. After six weeks, the ligature was removed under halothane anesthesia and a catheter (PE 60) with a cuff was placed in the dome of the bladder and secured with a purse string suture. The catheter was tunneled under the skin and exteriorized through an opening in the back of the neck. The abdominal incision was sutured and the free end of the catheter sealed. In order to prevent infections the rats received an injection of bicillin C-R (150000 units/rat). Two days later the animals were used in cystometrical evaluations. The animals were placed in the metabolic cages and the catheter was attached (using a "T" connector) to a Statham pressure transducer (Model P23Db) and to a Harvard infusion pump. A plastic beaker attached to a force displacement transducer (Grass FTO3) was placed under the rat's cage to collect and record urine volume. Animals were allowed 15–30 minutes to rest before the saline infusion (20 ml/hr for 20 minutes) was started for the first cystometry period. Two hours after the first cystometry period, the rats were dosed with the vehicle or the test compound and one hour later a second cystometry was performed.

The following urodynamic variables were recorded:

Basal bladder pressure = the lowest bladder pressure during cystometry
Threshold pressure = bladder pressure immediately prior to micturition
Micturition volume = volume expelled
Micturition pressure = peak pressure during voiding
Spontaneous activity = mean amplitude of bladder pressure fluctuations during filling Presentation of Results:

The mean value of each variable was calculated before and after compound administration. For each compound the changes in the variables measured were compared to the values obtained before treatment and expressed as percent inhibition. The data was also subjected to 2-way analysis of variance to determine significant ($p<0.05$) changes in the variable measured.

Criteria for Activity:

The most characteristic finding in this rat model was spontaneous bladder contractions which develop during filling. The compounds which inhibit spontaneous contractions by at least 50% at 10 mg/kg p.o. or i.v. (arbitrary chosen dose) were considered active.

The results of this study are shown in Table II:

TABLE II

Inhibition of Spontaneous Contractions In Vivo

| Compound | # of animals | dose mg/kg (iv) | % Red (F)* | % Red (A)** |
|---|---|---|---|---|
| Example 1 | 3 | 3 | −84 ± 8 | −54 ± 30 |

*percent reduction in the total number of spontaneous contractions in the hypertrophied rat bladder model
**percent reduction in the amplitude of spontaneous contractions in the hypertrophied rat bladder model Hence, it can be seen that the compounds of this invention have a pronounced effect on smooth muscle contractility and are useful in the treatment of urinary incontinence, irritable bladder and bowel disease, asthma, hypertension, stroke, and similar diseases as mentioned above, which are amenable to treatment with potassium channel activating compounds by administration, orally, parenterally, or by aspiration to a patient in need thereof.

The present invention may be embodied in other specific forms without departure from the spirit and essential attributes thereof and accordingly, reference should be made to the appended claims rather than to the foregoing as indicating the scope of the invention.

What is claimed is:

1. A compound of Formula I:

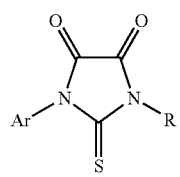

(I)

wherein:
R is branched lower alkyl; and
Ar is phenyl substituted with one or more of halogen, lower alkyl, lower alkoxy, lower alkylthio, lower alkylamino, cyano, or perfluoroalkoxy or a pharmaceutically acceptable salt thereof.

2. The compound of Formula I wherein:
R is $C_4$–$C_6$ branched lower alkyl; and
Ar is phenyl substituted with one or more halogen, cyano, or lower alkyl.

3. The compound of claim 1 which is 4-[4,5-Dioxo-2-thioxo-3-(1,2,2-trimethyl-propyl)-imidazolidin-1-yl]-benzonitrile.

4. The compound of claim 1 which is 4-[3-(2,2-Dimethyl-propyl)-4,5-dioxo-2-thioxo-imidazolidin-1-yl]-benzonitrile.

5. The compound of claim 1 which is 4-[3-(1,1-Dimethyl-propyl)-4,5-dioxo-2-thioxo-imidazolidin-1-yl]-benzonitrile.

6. The compound of claim 1 which is 4-(3-tert-Butyl-4,5-dioxo-2-thioxo-imidazolidin-1-yl)-benzonitrile.

7. The compound of claim 1 which is 4-[3-(1,1-Dimethyl-propyl)-4,5-dioxo-2-thioxo-imidazolidin-1-yl]-3-ethyl-benzonitrile.

8. The compound of claim 1 which is 4-[4,5-Dioxo-2-thioxo-3-((1R)-1,2,2-trimethyl-propyl)-imidazolidin-1-yl]-benzonitrile 3-[4,5-Dioxo-2-thioxo-3-(1,2,2-trimethyl-propyl)-imidazolidin-1-yl]-benzonitrile.

9. The compound of claim 1 which is 1-(4-Bromo-phenyl)-2-thioxo-3-(1,2,2-trimethyl-propyl)-imidazolidine-4,5-dione.

10. The compound of claim 1 which is 1-(4-Dimethylamino-phenyl)-3-(2,2-dimethyl-propyl)-2-thioxo-imidazolidine-4,5-dione hydrochloride.

11. The compound of claim 1 which is 1-(2,4-Difluoro-phenyl)-2-thioxo-3-(1,2,2-trimethyl-propyl)-imidazolidine-4,5-dione.

12. The compound of claim 1 which is 1-(4-Chloro-phenyl)-2-thioxo-3-(1,2,2-trimethyl-propyl)-imidazolidine-4,5-dione.

13. The compound of claim 1 which is 1-(2,4-Difluoro-phenyl)-3-(2,2-dimethyl-propyl)-2-thioxo-imidazolidine-4,5-dione.

14. The compound of claim 1 which is 1-(2,2-Dimethyl-propyl)-3-(4-fluoro-phenyl)-2-thioxo-imidazolidine-4,5-dione.

15. The compound of claim 1 which is 1-(4-tert-Butyl-phenyl)-2-thioxo-3-(1,2,2-trimethyl-propyl)-imidazolidine-4,5-dione.

16. A pharmaceutical composition comprising a pharmaceutically acceptable carrier and an effective amount of a compound of Formula I:

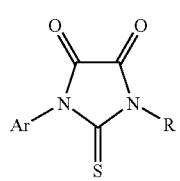

(I)

wherein:
R is branched lower alkyl; and
Ar is phenyl substituted with one or more of halogen, lower alkyl, lower alkoxy, lower alkylthio, lower alkylamino, cyano, or perfluoroalkoxy or a pharmaceutically acceptable salt thereof.

* * * * *